United States Patent
McCabe

(10) Patent No.: US 8,673,098 B2
(45) Date of Patent: Mar. 18, 2014

(54) METHOD AND APPARATUS FOR STRETCHING SEGMENTED STRETCHABLE FILM AND APPLICATION OF THE SEGMENTED FILM TO A MOVING WEB

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 236 days.

(21) Appl. No.: 12/925,570

(22) Filed: Oct. 25, 2010

(65) Prior Publication Data

US 2011/0094657 A1 Apr. 28, 2011

Related U.S. Application Data

(60) Provisional application No. 61/279,938, filed on Oct. 28, 2009.

(51) Int. Cl.
*A61F 13/15* (2006.01)

(52) U.S. Cl.
USPC .......................................... 156/163; 156/229

(58) Field of Classification Search
USPC ................................. 156/160, 164, 163, 229
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |

(Continued)

FOREIGN PATENT DOCUMENTS

| BE | 1007854 | 11/1995 |
|---|---|---|
| CA | 1146129 | 5/1983 |

(Continued)

OTHER PUBLICATIONS

USPTO Office Action dated Jun. 25, 2010 regarding U.S. Appl. No. 12/383,655, 24 pages.

(Continued)

*Primary Examiner* — Jeff Aftergut
(74) *Attorney, Agent, or Firm* — Ryan Kromholz & Manion, S.C.

(57) ABSTRACT

An elastic material is cut, set to a product pitch, stretched a desired amount and applied to a moving target web to create a product with a desired amount of elasticity over a desired area. A vacuum wheel with an aggressive vacuum pattern is used for securing and stretching the stretchable film, the same type of wheel also capable of being used as a trim removal device.

1 Claim, 11 Drawing Sheets

(56) References Cited

U.S. PATENT DOCUMENTS

| | | |
|---|---|---|
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerie |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,981,763 A | 9/1976 | Brocklehurst |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A * | 12/1982 | Radzins ................. 156/164 |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,479,836 A * | 10/1984 | Dickover et al. ............. 156/164 |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,578,133 A | 3/1986 | Oshefsky et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |

(56) References Cited

U.S. PATENT DOCUMENTS

| | | |
|---|---|---|
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vilet |
| 4,726,876 A | 2/1988 | Tomsovic |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | DesMarais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,203,043 A | 4/1993 | Riedel |
| 5,213,645 A | 5/1993 | Nomura et al. |
| 5,223,069 A | 6/1993 | Tokuno et al. |
| 5,226,992 A | 7/1993 | Morman |
| 5,246,433 A | 9/1993 | Hasse et al. |
| 5,267,933 A | 12/1993 | Precoma |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,674,334 A | 10/1997 | Instance |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A | 12/1997 | Hartman et al. |
| 5,707,470 A | 1/1998 | Rajala et al. |
| 5,711,832 A | 1/1998 | Glaug et al. |
| 5,725,518 A | 3/1998 | Coates |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,766,389 A | 6/1998 | Brandon et al. |
| 5,788,797 A | 8/1998 | Herrin et al. |
| 5,817,199 A | 10/1998 | Brennecke et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Borresent et al. |
| 5,964,970 A | 10/1999 | Woolwine et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,183,576 B1 | 2/2001 | Couillard et al. |
| 6,210,386 B1 | 4/2001 | Inoue |
| 6,212,859 B1 | 4/2001 | Bielik, Jr. et al. |

(56) References Cited

U.S. PATENT DOCUMENTS

| | | |
|---|---|---|
| 6,214,147 B1 | 4/2001 | Mortellite et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,587 B1 | 8/2001 | Borresen et al. |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,550,517 B1 * | 4/2003 | Hilt et al. .................. 156/557 |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,750,466 B2 | 6/2004 | Guha et al. |
| 6,766,817 B2 | 7/2004 | da Silva |
| 6,766,843 B2 | 7/2004 | Hilt et al. |
| 6,808,582 B2 | 10/2004 | Popp et al. |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,045,031 B2 | 5/2006 | Popp et al. |
| 7,066,586 B2 | 6/2006 | da Silva |
| 7,077,393 B2 | 7/2006 | Ishida |
| 7,130,710 B2 | 10/2006 | Popp et al. |
| 7,172,666 B2 | 2/2007 | Groves et al. |
| 7,214,174 B2 | 5/2007 | Allen et al. |
| 7,214,287 B2 | 5/2007 | Shiomi |
| 7,247,219 B2 | 7/2007 | O'Dowd |
| 7,303,708 B2 | 12/2007 | Andrews et al. |
| 7,347,914 B2 | 3/2008 | Umebayashi et al. |
| 7,380,213 B2 | 5/2008 | Pokorny et al. |
| 7,398,870 B2 | 7/2008 | McCabe |
| 7,452,436 B2 | 11/2008 | Andrews |
| 7,533,709 B2 | 5/2009 | Meyer |
| 7,537,215 B2 | 5/2009 | Beaudoin et al. |
| 7,618,513 B2 | 11/2009 | Meyer |
| 7,638,014 B2 | 12/2009 | Coose et al. |
| 7,640,962 B2 | 1/2010 | Meyer et al. |
| 7,703,599 B2 | 4/2010 | Meyer |
| 7,708,849 B2 | 5/2010 | McCabe |
| 7,770,712 B2 | 8/2010 | McCabe |
| 7,780,052 B2 | 8/2010 | McCabe |
| 7,811,403 B2 | 10/2010 | Andrews |
| 7,861,756 B2 | 1/2011 | Jenquin et al. |
| 7,909,956 B2 | 3/2011 | Coose et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews et al. |
| 8,011,493 B2 | 9/2011 | Giuliani et al. |
| 8,016,972 B2 | 9/2011 | Andrews et al. |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0087425 A1 | 5/2004 | Ng et al. |
| 2004/0112517 A1 | 6/2004 | Groves et al. |
| 2004/0164482 A1 | 8/2004 | Edinger |
| 2004/0167493 A1 * | 8/2004 | Jarpenberg et al. .......... 156/164 |
| 2005/0000628 A1 | 1/2005 | Norrley |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 * | 12/2005 | Beaudoin et al. .......... 271/10.01 |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2006/0266465 A1 | 11/2006 | Meyer |
| 2007/0074953 A1 | 4/2007 | McCabe |
| 2008/0223537 A1 | 9/2008 | Wiedmann |
| 2009/0020211 A1 | 1/2009 | Andrews et al. |
| 2010/0078119 A1 | 4/2010 | Yamamoto |
| 2010/0078120 A1 | 4/2010 | Otsubo |
| 2010/0078128 A1 | 4/2010 | Yamamoto et al. |
| 2010/0193138 A1 | 8/2010 | Eckstein et al. |
| 2010/0193155 A1 | 8/2010 | Nakatani et al. |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| CA | 2337700 | 8/2008 |
| CA | 2407867 | 6/2010 |

(56) References Cited

FOREIGN PATENT DOCUMENTS

| | | |
|---|---|---|
| DE | 60123502 | 10/2006 |
| DE | 60216550 | 12/2006 |
| DE | 102006047280 | 4/2007 |
| EP | 0044206 | 1/1982 |
| EP | 0048011 | 3/1982 |
| EP | 509706 | 11/1982 |
| EP | 0089106 | 9/1983 |
| EP | 520559 | 12/1983 |
| EP | 0206208 | 12/1986 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1366734 | 12/2003 |
| EP | 1571249 | 9/2005 |
| EP | 1619008 | 1/2006 |
| EP | 1707168 | 4/2006 |
| EP | 1302424 | 12/2006 |
| EP | 1801045 | 6/2007 |
| EP | 1994919 | 11/2008 |
| EP | 2036522 | 3/2009 |
| EP | 2233116 | 9/2010 |
| EP | 2238955 | 10/2010 |
| ES | 296211 | 12/1987 |
| ES | 200601373 | 7/2009 |
| ES | 2311349 | 9/2009 |
| FR | 2255961 | 7/1975 |
| FR | 1132325 | 10/2006 |
| FR | 2891811 | 4/2007 |
| GB | 191101501 | 0/1912 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 439897 | 8/1990 |
| GB | 428364 | 1/1992 |
| GB | 2288316 | 10/1995 |
| IT | 1374910 | 5/2010 |
| IT | 1374911 | 5/2010 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 9299398 | 11/1997 |
| JP | 10035621 | 2/1998 |
| JP | 10-277091 | 10/1998 |
| SE | 0602047 | 5/2007 |
| SE | 0601003-7 | 6/2007 |
| SE | 0601145-6 | 10/2009 |
| WO | WO 2008155618 | 12/1988 |
| WO | WO 97/22317 A1 | 6/1997 |
| WO | WO9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |
| WO | WO 2007029115 | 3/2007 |
| WO | WO 2007039800 | 4/2007 |
| WO | WO 2007126347 | 11/2007 |
| WO | WO 2008001209 | 1/2008 |

OTHER PUBLICATIONS

USPTO Office Action dated Dec. 1, 2010 regarding U.S. Appl. No. 12/383,655, 16 pages.
USPTO Office Action dated Apr. 2, 2008 regarding U.S. Appl. No. 11/112,160, 56 pages.
European Search Report, regarding European Appln. No. 10250536.9, dated May 10, 2010, 2 pages.
Reciprocating Mechanisms, Ingenious Mechanisms for Designers and Inventors, Franklin Jones vol. 1, date unknown, 2 pages.

* cited by examiner

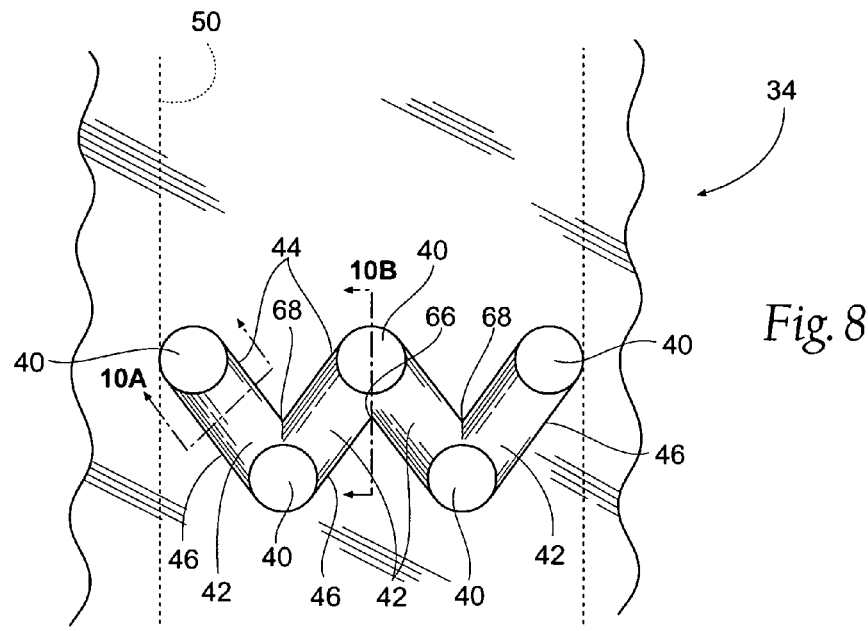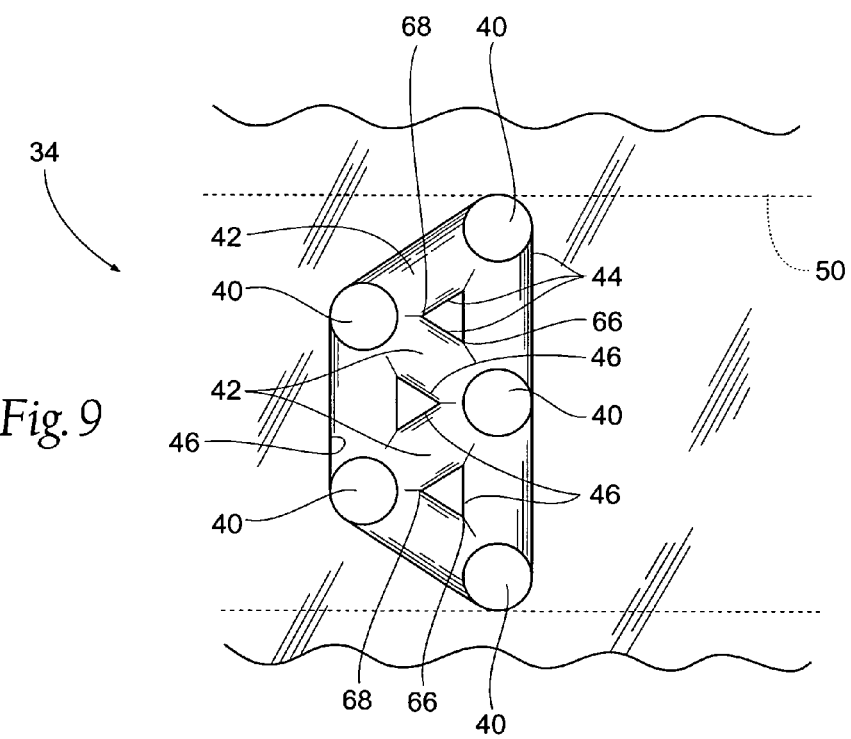

METHOD AND APPARATUS FOR STRETCHING SEGMENTED STRETCHABLE FILM AND APPLICATION OF THE SEGMENTED FILM TO A MOVING WEB

RELATED APPLICATION

This application claims the benefit of U.S. Provisional Patent Application Ser. No. 61/279,938, filed 28 Oct. 2009.

BACKGROUND OF THE INVENTION

This invention relates to segmenting and stretching stretchable materials and coupling the segmented stretched material to an unstretched material to create a stretchable laminate. Such a stretchable combination of materials can be used in any number of applications, such as feminine hygiene products, diapers, apparel, or textiles.

Sanitary napkins used in feminine hygiene are absorbent items worn by women to recover undesirable bodily discharges. These absorbent articles are typically comprised of an absorbent core sandwiched between layers of woven or non-woven materials.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper (and, oftentimes also in conjunction with feminine hygiene products), multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Generally, disposable undergarments such as pants-type diapers are made up of two nonwoven layers of material with elastic strands of material placed between the two nonwoven layers of material thus creating an elastic web laminate. The layers of material are continuous sheets of material that are eventually cut into individual undergarment lengths. The elastic strands may be arranged and cut so that specific areas of the undergarment are free of elastic tension or forces. An absorbent pad, often contained within an insert or core is then also placed into the pants-type diaper product.

To insure the pants-type diaper retains a proper shape and to hold all of the added layers of the diaper, reinforcing layers and backing materials are normally added to the continuous sheets of material, with the reinforcing layers corresponding to the cut elastic strands of each individual blank. Each of these layers needs to be adhesively joined at some point in the manufacturing process to the elastic web laminate to form the completed undergarment.

Often, void spaces need to be created in the diaper, such as holes cut out of the main web for provided leg holes when the undergarment is ultimately formed. To create the void spaces, the web is ordinarily die cut, with the web severed between a die and an anvil. The portion of the web material that is removed is referred to as a "chip." As the die wears throughout time, the severing of the chip from the web material becomes gradually a duller cut. This complicates the removal of the chip because the severing might not create a continuous cut out chip, with possibly some strands of the web material still coupling the chip with the web. It is desired to lengthen the amount of time and increase the number of chips that a single die can effectively be used for, to reduce the number of die change-outs.

The current practice in applying a stretchable web such as a poly web to a second web involves continuously feeding the poly web into the process which results in poly running full length of product, or alternatively, full length of a constructed insert core which is then placed onto a nonwoven-type chassis. Not all machine configurations can be adapted from a full length poly chassis to a poly insert configuration due to space and/or cost restrictions. It should be understood that application of the poly web along the entire length of the product, rather than only where it is useful, increases the amount of poly material which must be utilized. This is a waste of the material resource and adds additional cost to the product. It is therefore desirable to create a lower cost product by putting stretchable material into the product only where it is useful, instead of the complete product.

This invention relates to the art of vacuum wheels and more particularly to a vacuum wheel vacuum opening configuration that has improved vacuum holding power to hold articles in place.

A vacuum wheel in the form of a rotary member having vacuum holes opening onto a cylindrical outer surface for the support and retention of stretchable film is typically a component of an apparatus that is known for various applications. A common example where an apparatus including a vacuum wheel would be used includes the construction of apparel that is worn on the body such as disposable diapers. In this application, an elastic waistband is stretched before being inserted into the waistband region. An example of such an apparatus is described in U.S. Pat. No. 4,925,520, commonly owned by the assignee hereof and incorporated herein by reference.

It is a common problem in such devices to experience insufficient vacuum holding strength for the materials to be held in place in relation to the shear forces applied to the materials. Another problem, where vacuum slots are used to improve the vacuum holding strength, is the loss of vacuum pressure along an edge of the vacuum slot. The vacuum holding force is a function of the area under the vacuum and the edges of the vacuum openings and slots against which the forces are applied. Simple round holes must be kept small in diameter to prevent the film from being sucked deep into the vacuum openings. The small area limits the holding force, and the small size limits the working edge length.

Various approaches have been taken for retaining flexible materials on a vacuum wheel. One approach has been to increase the number of vacuum openings on the available surface of the vacuum wheel. This can cause the size of the vacuum wheel to exceed possible size requirements for use in an apparatus. Examples of the use of a chevron pattern for improved grip are shown in U.S. Pat. No. 7,537,215, which is commonly owned by the assignee hereof and incorporated herein by reference.

SUMMARY OF THE INVENTION

In general terms, the invention comprises acting upon an elastic material by the steps of cutting, setting to a product pitch, stretching, and applying the elastic material to a moving target web. Any type of stretch engine, such as foam, poly, film, laminate, ribbon, indeed any type of elastic material whatsoever, can be used in the present method to form a stretchable material.

The methods of the present invention can be performed on elastic material presented as narrow as wide as necessary for the particular application. Stretched elastic in the machine direction provides elasticity for a discrete portion of a web that the elastic material is applied to.

The elastic material formed by the present invention ordinarily results in a component that can be used, for instance as a cuff elastic, a leg elastic, a waistband elastic, or on feminine hygiene products to provide a body conforming shape and fit. In other cases, the elastic material formed by the present invention can be used at any place where gathering is desirable, for instance at locations in products where particular body conformance is desirable. Different applications of the elastic material formed by the present invention can be applied in different patterns to result in different and variable product geometries.

Wheels of the present invention can be used either with or without removable shoes containing a vacuum array. Shoes, in some applications, might assist size change if different geometries of elastic materials are desired. For instance, if a newborn product on a machine, a smaller product might be necessary. The shoe can be sized to the length of stretch of the elastic piece applied to the product.

The step of cutting can take place on a cut/slip type mechanism, or any other process suitable for processing webs. The step of setting the severed elastic material to a product pitch can also take place on the cut/slip mechanism, or can take place by transferring the severed elastic material to a first rotating body referred to as a "set pitch" wheel. The step of stretching can take place by transferring the severed elastic to a second rotating body referred to as a "set stretch" wheel, the stretching caused by a difference in tangential speed of the "set pitch" and "set stretch" wheels, the "set stretch" wheel having a higher tangential speed to thereby cause the severed elastic member to stretch. Next, the stretched severed elastic member is applied to a moving target web. The moving target web containing individual stretched severed elastic member can then be processed downstream as desired to serve the needs of the particular desired product configuration.

The step of setting the severed elastic material to a product pitch using the "set pitch" wheel as opposed to merely using the slip/cut mechanism is though to improve registration window, or require less vacuum to achieve the desired stretch, but use of the slip/cut mechanism itself to set the product at pitch is likewise within the scope of the invention.

It has been found that the holding strength of a vacuum is strongly related to the shape of the vacuum pattern. By using a preferred pattern to give a favorable orientation relative to the force applied, the holding strength can be maximized to impart holding strength and ultimately apply stretch to the material.

Preferably but not necessarily, a multi-chevron or zig-zag pattern to improve the holding power. The chevron, or "W" pattern, provides increased holding area and increased edge length, and also provides for holding the film along several inside and outside corners, which tend to tighten, rather than loosen their grip when subject to high shear forces.

In another aspect, the present invention provides a vacuum wheel with improved vacuum holding strength capable of removing chips of material from running webs. The apparatus and methods of the present invention can be used for trim removal applications to grab hold of a trim piece and aggressively remove it from a web. Chip or trim removal is discussed in U.S. patent application Ser. No. 11/436,274, which shares ownership with the present application, and which disclosure is incorporated by reference as if fully set forth herein.

BRIEF DESCRIPTION OF THE DRAWINGS

FIG. 8 is a plan view of a chevron vacuum opening pattern that can be embodied on the vacuum wheel shown in FIGS. 5A-6.

FIG. 9 is a plan view of an alternative vacuum opening pattern.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

It is noted that the present techniques and apparatus are described herein with respect to disposable products such as diapers, but as previously mentioned, can be applied to a wide variety of processes in which discrete components are applied sequentially.

Figure 1A:
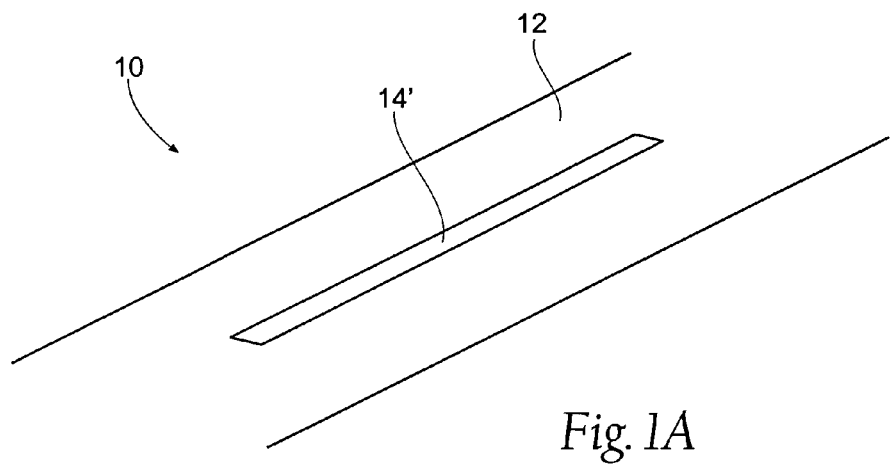
FIG. 1A is a perspective view of a tensioned product formed by the methods of the present invention.

FIG. 1 is a perspective view of a tensioned product 10 formed by the methods of the present invention. A segment 14' of elastic material is coupled to a web of material 12, such as a non-woven material used commonly in manufacture of disposable products.

Figure 1B:
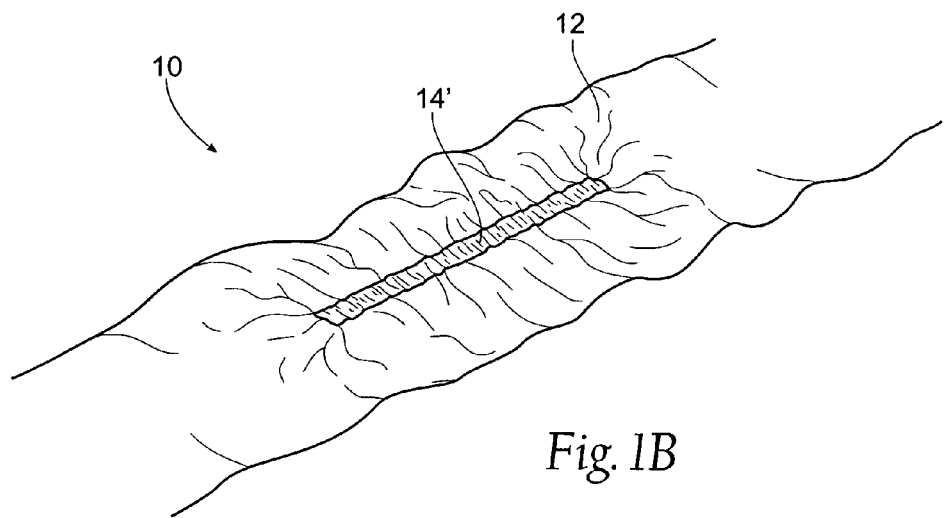
FIG. 1B is a perspective view of a slack product formed by the methods of the present invention.

Referring now to FIG. 1B, a perspective view of a slack product 10 formed by the methods of the present invention is shown. As can be seen, tension has been removed from the web of material 12 and elastic segment 14', such as by severing the web 12 before and/or after the elastic segment 14' to create a stretchable segment of material, the elastic segment 14' imparting the stretch characteristic to materials that are not necessarily stretchable, such as non-woven webs of material.

Figure 2:
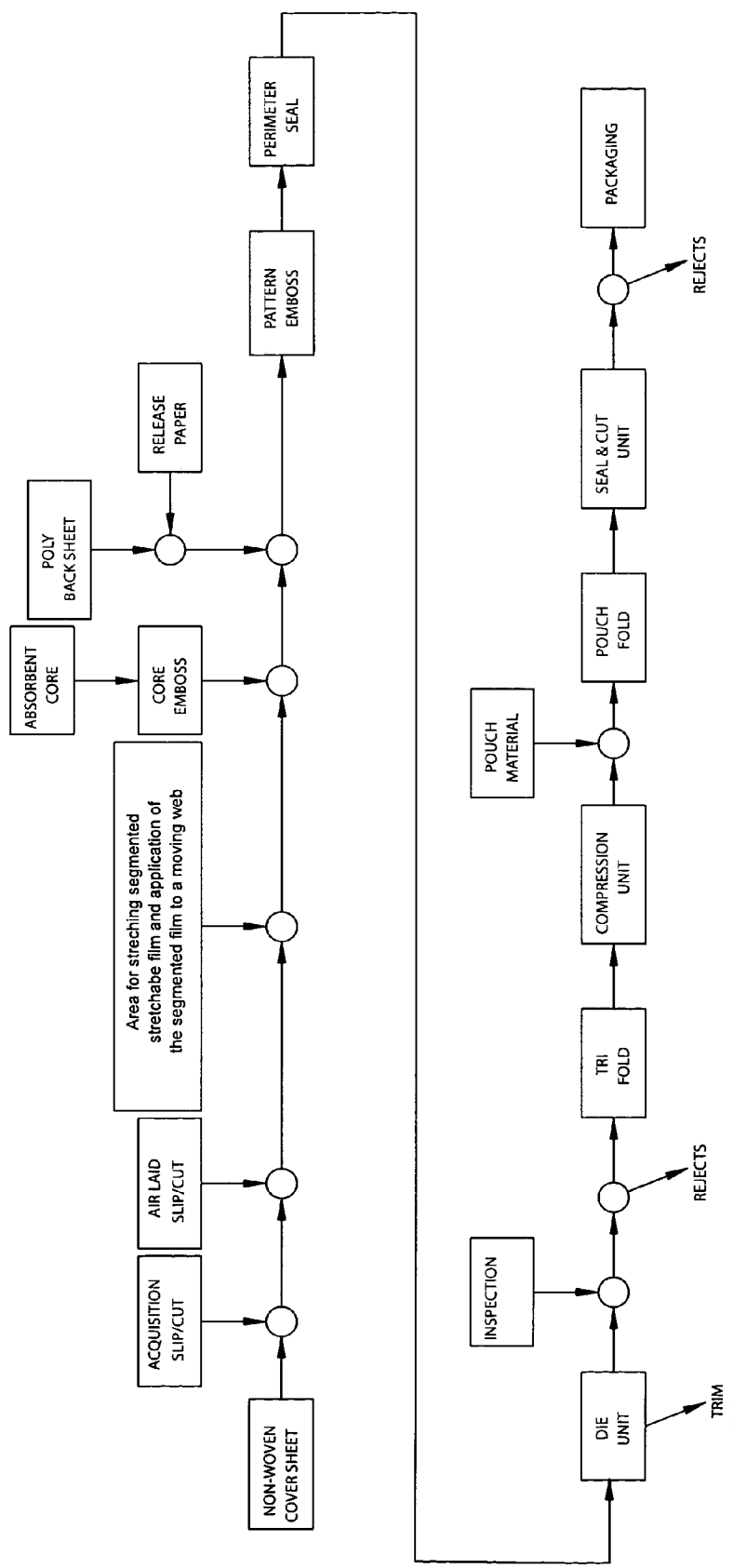
FIG. 2 show a schematic representation of the manufacture of feminine hygiene products.

Referring now to FIG. 2, a schematic representation of formation of a feminine hygiene product is shown.

Absorbent articles including bandages, disposable diapers, and sanitary napkins, generally include an absorbent core that has a multiplicity of components so as to improve the article's absorption and retention characteristics. These absorbent cores have had their total absorbency improved greatly by the addition of super absorbent material to the commonly used absorbent fibrous materials. Although absorbent articles containing absorbent cores are one potential application of the present invention, it is understood that the invention is broader in application that just disposable or absorbent products, and can be utilized in other processes, such as during formation of single-use disposable items that do not contain a fluff-forming component.

Typically, the absorbent fibrous material is composed of cellulose wadding or cellulosic wood pulp material commonly referred to as "fluff", although a mixture of natural and synthetic fibers is within the scope of the invention. An absorbent core composed of wood pulp fluff is typically formed by employing conventional air laying techniques. As shown in FIG. 2, the core can be individually pre-formed.

Insert material is optionally coupled to the absorbent core, which becomes sandwiched between a preferably poly backsheet and a non-woven cover sheet. In an exemplary embodiment of the present invention, the segmented and stretched elastic component is coupled to the non-woven cover sheet in desirable areas, for instance where a gather is desired or where a body-conforming shape or feel is desired. By way of example, the cut, stretched elastic member can be applied to a moving web at the areas shown in FIG. 2 within the highlighted region of the process, to result in the elastic material contained within a sandwich of backsheet and cover sheet materials, and if desired, the sandwich also containing an absorbent core.

The backsheet/insert/core/elastic/coversheet sandwich is then further processed to its desired size and shape by a series of cutting, compression, and trim removal steps as shown. The backsheet/insert/core/elastic/coversheet sandwich can also be coupled to a pouch material for individual packaging, folded, and then packaged in groups for resale if desired.

Referring now to FIGS. 3A-3E, schematic representations of one embodiment of an apparatus for forming a product 10 by the methods of the present invention are shown.

Figure 3A:
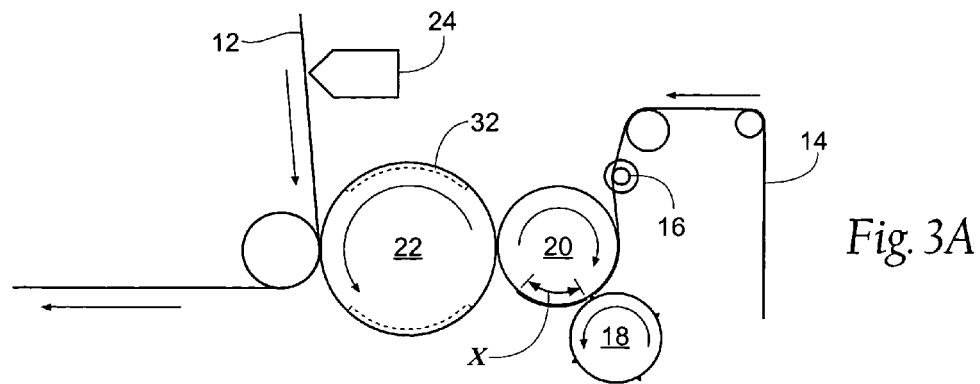
FIGS. 3A-3E are a schematic representation of one embodiment of an apparatus for forming a product by the methods of the present invention.

Referring to FIG. 3A, a web 14 of material, such as a stretchable or elastic material is fed to clamp collar 16 used to stabilize the web 14 laterally to minimize slippage of the web 14 in the cross-machine direction. It is noted that web 14 may have undergone slitting and separating prior to this point, if desired.

Figure 3B:
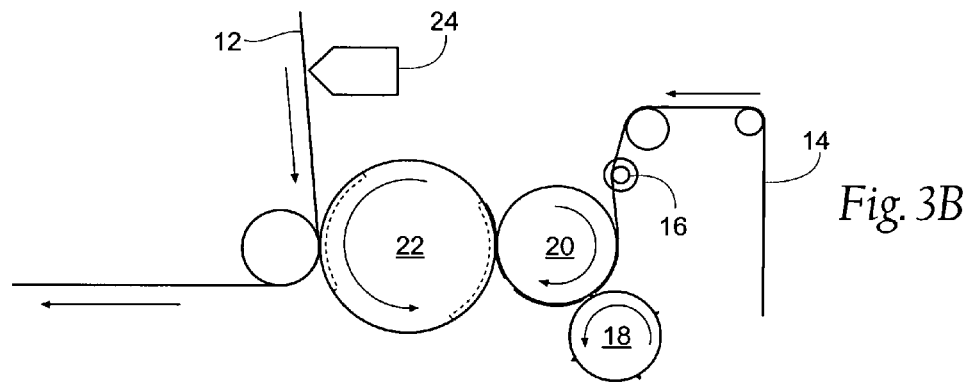

Referring to FIG. 3B, in the illustrated embodiment the slip/cut unit comprises an anvil roll 20 and a knife roll 18. The anvil 20 is preferably a vacuum anvil. The web 14 is fed against the anvil 20 surface and is cut into segments 14' by the knife roll 18. With regard to the embodiment depicted, roll 20 is a preferably slip-cut anvil that also provide the re-pitch component of the process described herein.

In the first series of schematics shown by FIGS. 3A-3E the segments 14' are cut onto the anvil roll 20 at product pitch to a length X. Next, referring to FIG. 3B, the segments 14' are introduced to the "set stretch" rotating vacuum wheel 22 having vacuum commutation regions 32. As the set stretch wheel 22 is rotated, vacuum applied near the leading edge of vacuum commutation regions 32 grabs the leading edge of segments 14' while the segments 14' are still retained by vacuum on the anvil roll 20 (or, as will be described later with reference to FIGS. 4A-4G, still retained by the "set pitch" wheel 26) at the trailing edges of segments 14'.

Figure 3C:
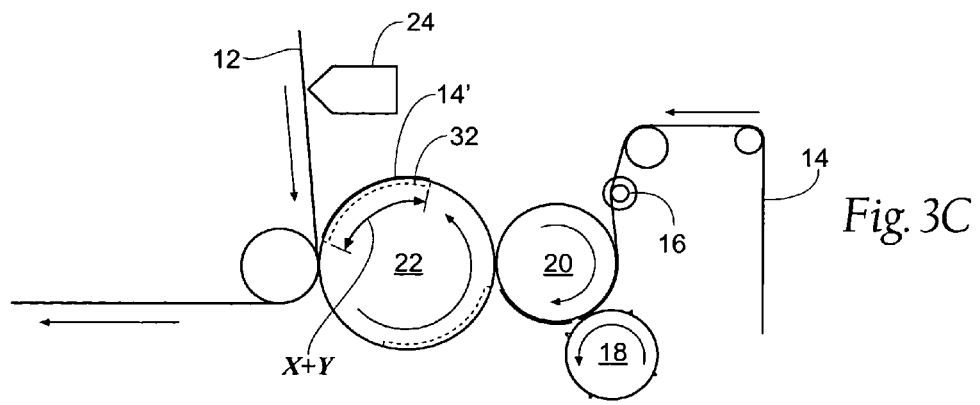

Referring to FIG. 3C, segments 14' are stretched by a difference in tangential speed of the set stretch wheel 32 and the anvil 20 to a length of X+Y. The larger the difference in tangential speed between the two, the larger the amount of stretch.

Figure 3D:
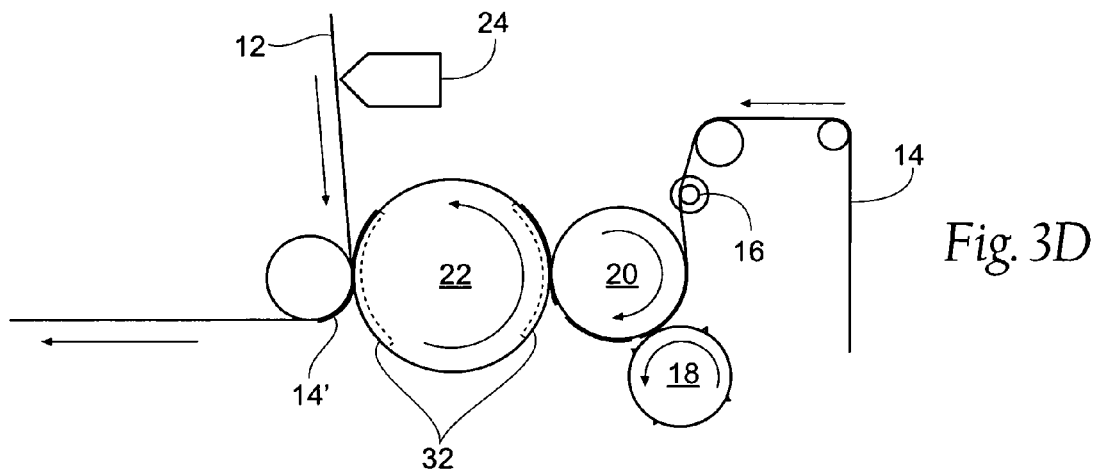
Figure 3E:
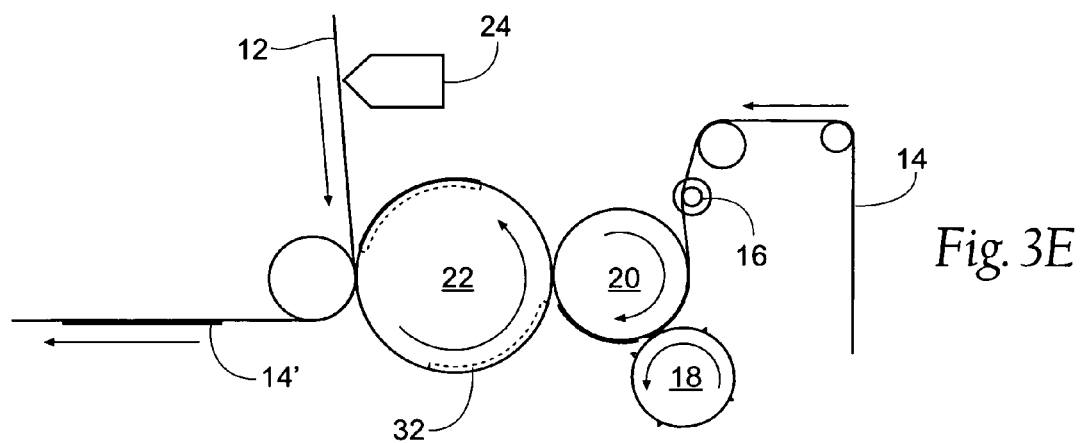
Figure 4A:
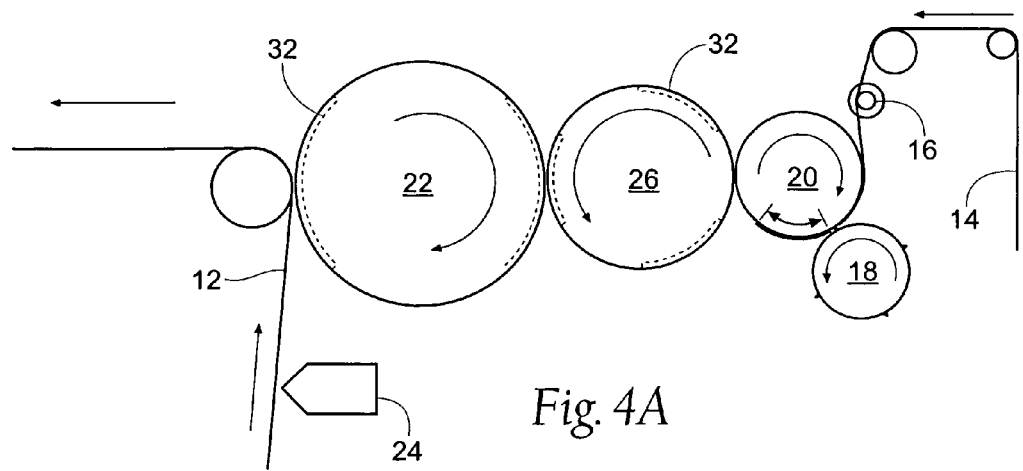
FIGS. 4A-4G are a schematic representation of a second embodiment of an apparatus for forming a product by the methods of the present invention.
Figure 4B:
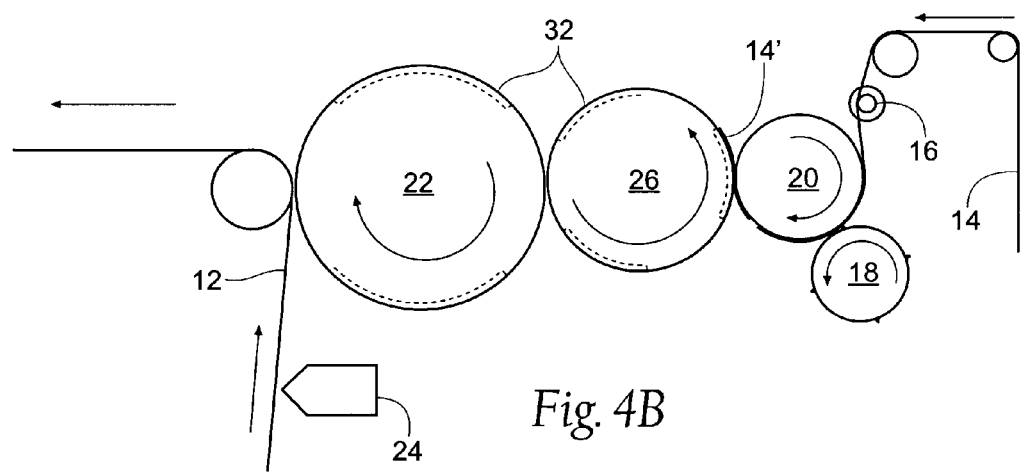
Figure 4C:
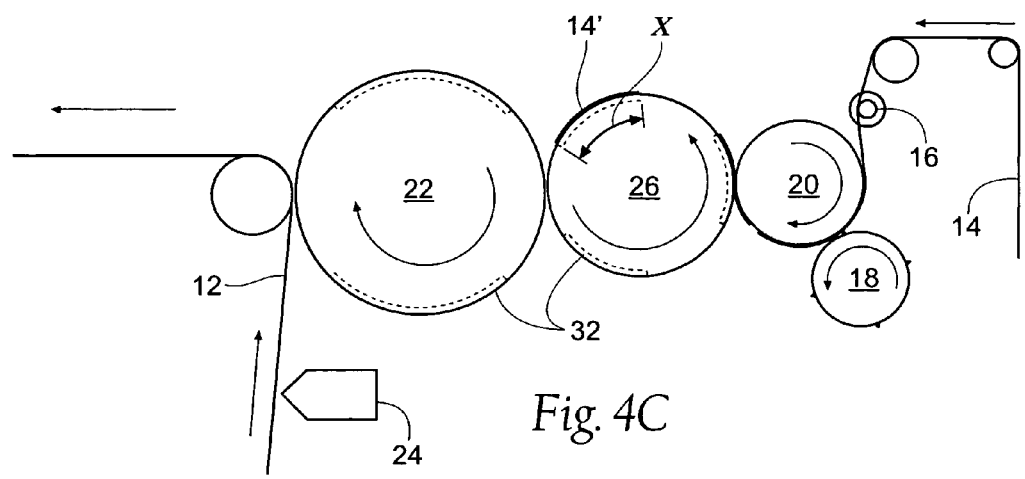
Figure 4D:
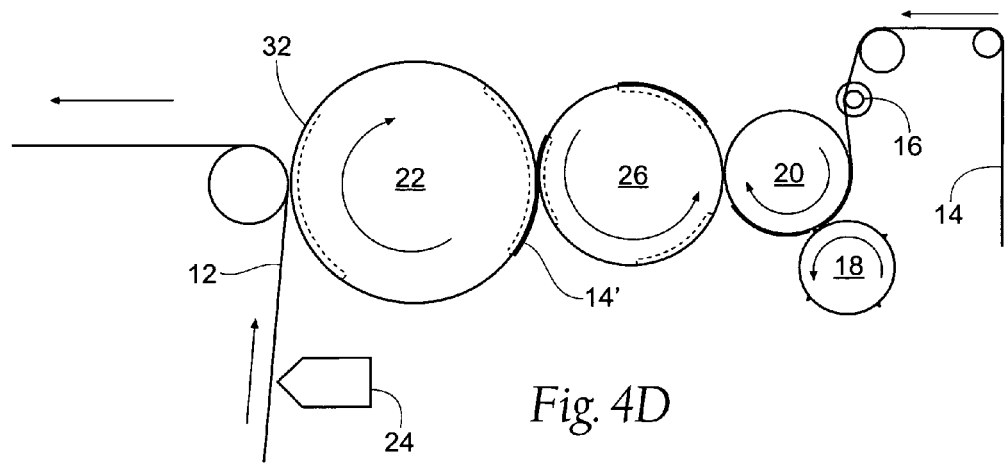
Figure 4E:
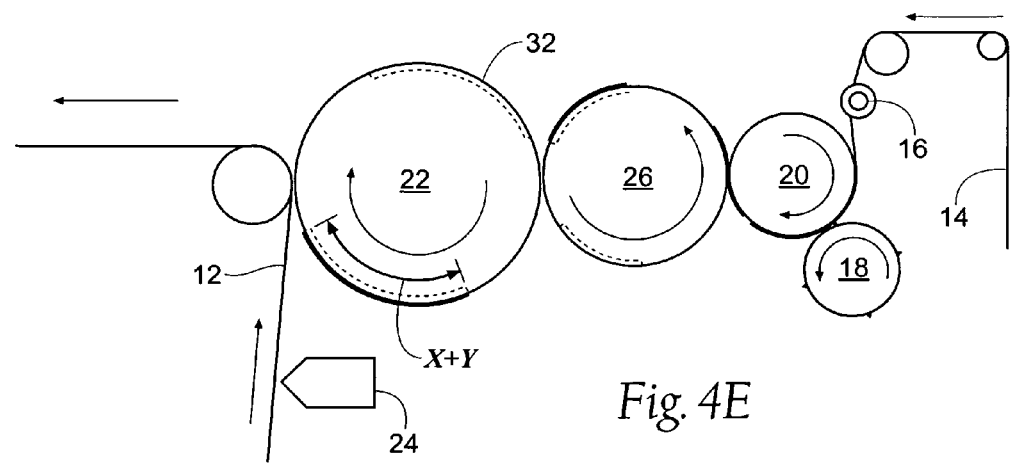
Figure 4F:
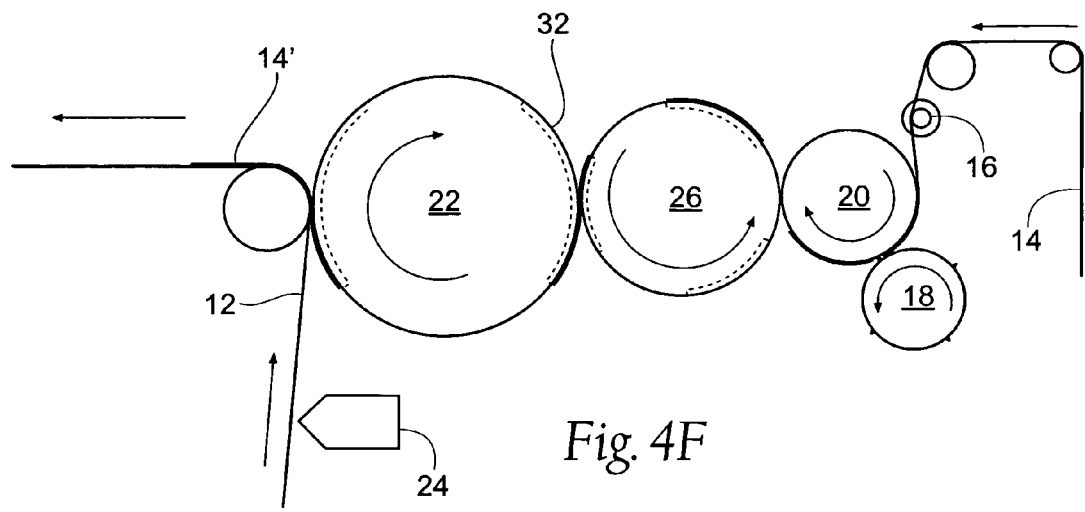
Figure 4G:
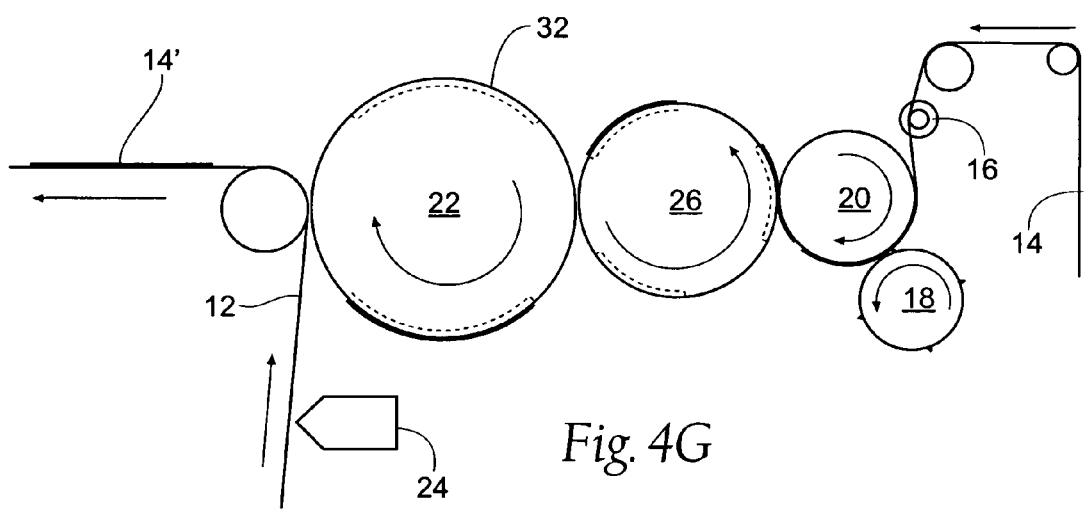

Referring now to FIGS. 3D and 3E, next, the stretched severed elastic members 14' are applied to a moving target web 12.

It is contemplated that the segments 14' may be secured to the target web 12 in any manner known in the art. For example, and not by way of limitation, an adhesive may be applied to the surface of the web 12 such as by an adhesive applicator 24 of any type known in the art (or, to the segmented and stretched segments 14').

Alternatively, other bonding techniques such as ultrasonic bonding, or heat bonding stations could also be employed.

The moving target web 12 containing individual stretched severed elastic member 14' can then be processed downstream as desired to serve the needs of the particular desired product configuration.

Referring now to FIGS. 4A-4G, a schematic representation of a second embodiment of an apparatus for forming a product by the methods of the present invention is shown. In this preferred technique, the step of setting the severed elastic material 14 to a product pitch uses a "set pitch" wheel 26 as opposed to merely using the slip/cut mechanism 18/20. This technique is believed to improve registration window, and require less vacuum to achieve the desired stretch, but use of the slip/cut mechanism itself to set the product at pitch is likewise within the scope of the invention.

Referring to the set pitch wheel 26, the configuration shown is known as a "3-up" wheel, because there is shown three zones 32 of vacuum commutation. M is noted that the set stretch roll 22 of the illustrated embodiment is shown as a "2 up" roll, and the differences and the geometries of the two rolls result in different tangential speeds on the surfaces of the two rolls 22 and 26.

The circumferential distance between the leading edges of the vacuum commutation zones 32 on the set pitch roll 26 define the product pitch. Product pitch generally refers to a length of material that runs the full length of the product under production. A product pitch for typical diaper products varies between infant to toddler to adult diapers, but can be thought of as a machine direction distance between two like components on a running web of material.

The purpose of the set-pitch roll 26 is to define the distance between leading edges of the like-components on the final product. The set-pitch roll 26 sets the pitch of the elastic engine.

The set stretch roll 22 defines the amount of stretch applied to the segments 14'. A large difference in the tangential speed of the set stretch roll 22 and the set pitch roll 26 results in a large degree of stretch. Likewise, if the set stretch roll 22 and the set pitch roll 26 have the same tangential speed, there would be no additional stretch imparted to the segments 14'.

In this manner, the preferred embodiment illustrated in FIGS. 4A-4G allows exact duplication of distance between leading edges of the segments 14' when they are eventually applied to moving web 12, as well as exact duplication and definition of the amount of stretch applied to each segment 14'. For instance, one can design a product with a 5" length of relaxed material stretchable to a length of 7", to define the amount of stretch percentage. The leading edge of segments 14' will have been grasped and stretched by the set stretch roll 22, while the trailing edge is still retained by the vacuum commutation ports provided on the set pitch roll 26.

In alternative embodiments (not shown), additional re-pitch rolls 26 and additional stretch rolls 22 may be employed to either re-pitch or to further stretch the material as necessary. For instance, if stretching is desired to be performed further sequentially, in order to facilitate introduction of additional components into the web, additional stretch rolls 22 may be employed either adjacent to or downstream of the stretch roll 22 shown. Likewise, additional re-pitch rolls 26 may be introduced adjacent to or downstream of the pitch roll 26 shown.

Figure 5A:
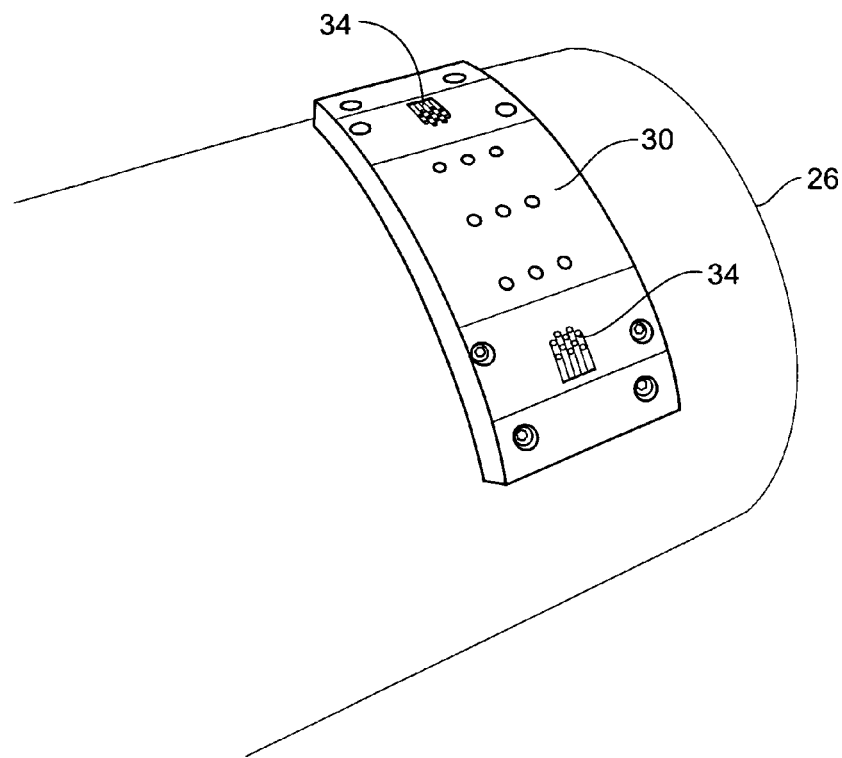
FIG. 5A is a perspective view of a vacuum wheel of the present invention incorporating a shoe carrying a vacuum array.

FIG. 5A is a perspective view of a representative vacuum wheel of the present invention such as set pitch roll 26 (shown) or set stretch roll 22 (not shown, though the formation would be similar). This embodiment incorporates a shoe 30 carrying a vacuum array 34. Vacuum arrays 34 are preferably provided to carry a leading edge of a segment 14' and a trailing edge of segment 14'. The distance between successive leading edge vacuum arrays 34 on a product pitch roll should preferably be at product pitch.

The end surface of roll 26 (shown on FIG. 6) includes a plurality of vacuum openings 50 spaced apart from each other through which vacuum is drawn. Vacuum source is applied to roll 26 by placing a fixed vacuum manifold assembly very close to end surface of roll 26 (preferably 0.005"±0.002" gap), and the vacuum is commuted through openings 50, to channels 48, ultimately to the vacuum array 34.

Figure 5B:
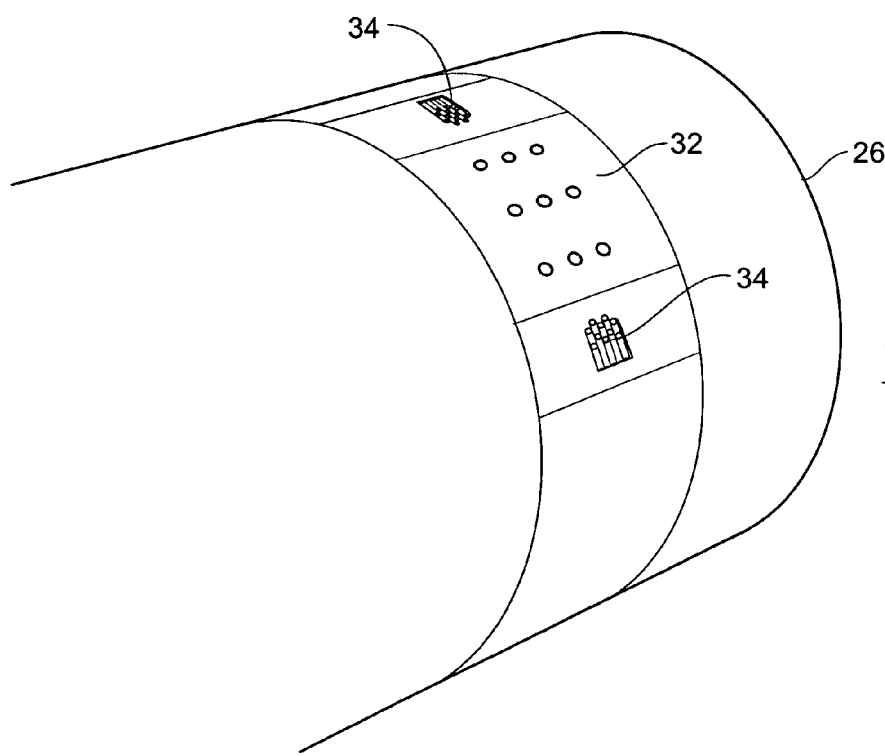
FIG. 5B is a perspective view of an alternate embodiment of a vacuum wheel of the present invention incorporating inserts as opposed to shoes as shown in FIG. 5A.

FIG. 5B is a perspective view of an alternate embodiment of a vacuum wheel of the present invention incorporating inserts 32 as opposed to shoes as shown in FIG. 5A. The inserts 32 are mounted to a surface of the roll 26. The vacuum wheels of the present invention preferably have a plurality of longitudinal vacuum ports 50 formed through them that may be parallel to but offset from an axis of rotation of the vacuum wheels. The vacuum ports 50 are preferably configured to connect to an external vacuum source (not shown). Extending generally radially outwardly from the vacuum ports 50 are vacuum passageways 48. Each vacuum passageway 48 extends from the vacuum port 50 to the vacuum opening 40 on the outer surface 22 of the vacuum wheel 20.

The vacuum wheels shown in FIGS. 5A and 5B also have utility as chip or trim removal devices if positioned and operated as such a device. FIG. 2 shows one step in an operation in which trim removal might be useful. In order to remove chips, the tangential speed of the wheels would be of a magnitude sufficient to rip one portion of material web from another portion of a material web. In this sense, and for illustrative purposes only, if the set-stretch roll 32 shown in FIG. 4F had a tangential speed of a great enough increase over the tangential speed of the set pitch roll 26, the set-stretch roll 32 could effectuate a ripping of an undesired portion of the incoming web if desired. In such an embodiment, the undesired portion of the incoming web could be discarded or recycled. An aggressive vacuum array 34, such as shown in FIGS. 8 and 9, would assist in providing an aggressive grasp on the incoming web and therefore assist in achieving the gripping and ripping forces necessary to rip the undesired web portion away.

Figure 7:
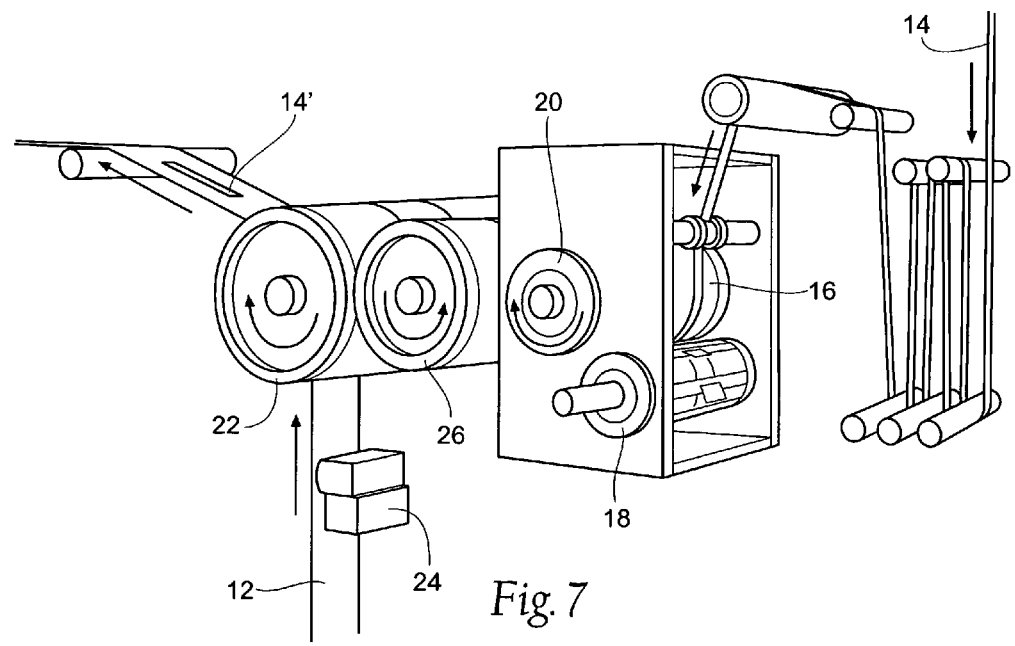
FIG. 7 is a perspective view of the second embodiment of an apparatus for forming a product by the methods of the present invention.

Referring now to FIG. 7, a perspective view of the embodiment shown in FIGS. 4A-4G is shown. There, an accumulator is shown introducing the web 14 into the unit, but an accumulator is not necessary, and any method or apparatus of introducing the material 14 into the process can be used.

Figure 6:
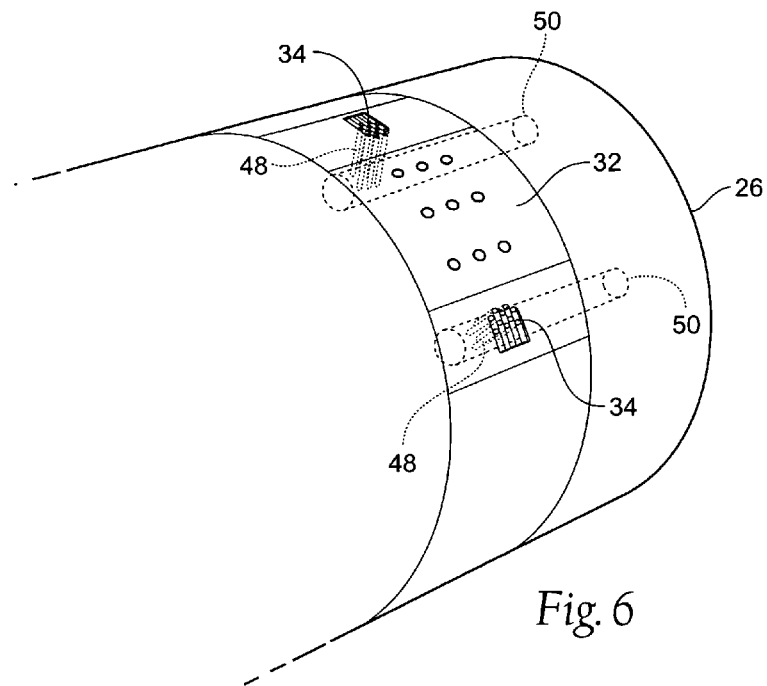
FIG. 6 is a perspective view of an alternate embodiment of a vacuum wheel of the present invention showing the method of vacuum commutation.

Referring now to FIG. 8, a plan view of a chevron vacuum opening pattern that can be embodied on the vacuum wheel shown in FIGS. 5A-6 is shown.

The vacuum openings 40 are preferably in vacuum contact with each other by way of vacuum slots 42, which are slots or grooves within the outer peripheral surface 22 of the vacuum wheel 20. These vacuum slots 42 may be milled or formed, and preferably provide vacuum contact between at least two vacuum openings 40. The vacuum slots 42 are adapted to have a first edge 44 and a second edge 46. In a preferred embodiment, the vacuum openings 40 and vacuum slots 42 define a chevron or zig-zag pattern (see FIG. 8), although other advantageous patterns are within the scope of this invention (for example, FIG. 9—also a chevron, but with additional slots).

As best seen in FIGS. 6 and 8, the vacuum openings 40 in conjunction with the vacuum slots 42 are adapted to attract and retain under the influence of vacuum segments 14'. When a vacuum is applied to the rolls 20, 22 and 26 (vacuum source not shown) and a web 14 or segments 14' are placed over the vacuum openings 40 and vacuum slots 42, the vacuum will attract and retain the web 14 or segments 14' on the outer surface of the rolls 20, 22 and 26.

In addition to the retaining vacuum force 64, the advantageous vacuum opening 40 and vacuum slot 42 chevron pattern provides a number of inside 66 and outside 68 corners. These inside 66 and outside 68 corners create additional inside corner forces 67 and outside corner forces 69. The inside 67 and outside 69 corner forces provide increased holding area, and tend to tighten, rather than loosen their grip when subject to high shear forces. The chevron or zig-zag pattern of vacuum openings 40 and vacuum slots 42 seen in FIGS. 3a and 3b takes advantage of these vacuum retaining forces 64, 67, and 69 to hold the web 14 or segments 14' in place, yet allows for the web 14 or segments 14' to slip over the vacuum openings 40 and vacuum slots 42 when the shear force applied to the segment of film 60 is stronger than the retaining vacuum forces 64, 67, and 69 on the web 14 or segments 14'.

FIG. 9 is a plan view of an alternative vacuum opening pattern. It is noted that the different contact (or gripping) surfaces/methods can be used depending on the type of elastic material being processed. The inserts 32 or shoes 34 can be configured for a belt method or for a pad method. A pad method might provide a sandpaper surface, a silicone rubber surface, a surface with pins protruding, etc.

Figure 10A:
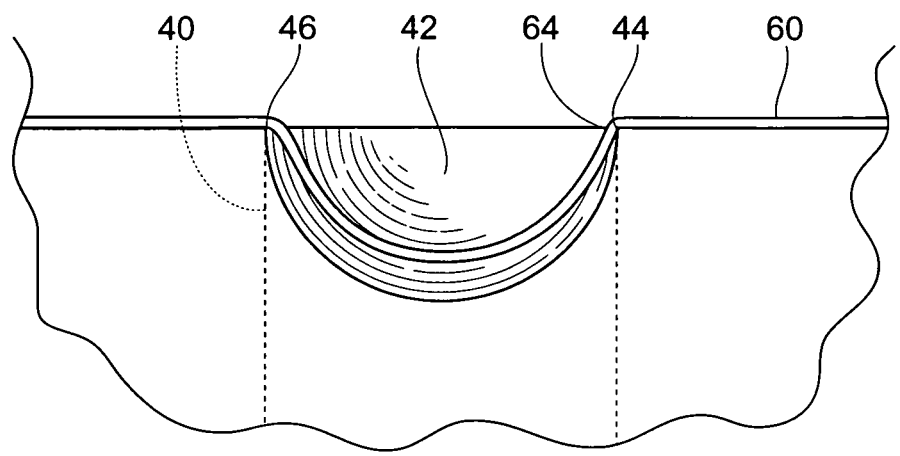
FIGS. 10A and 10B are a side elevation views, with portions cut away, of the vacuum wheel shown in FIG. 8.
Figure 10B:
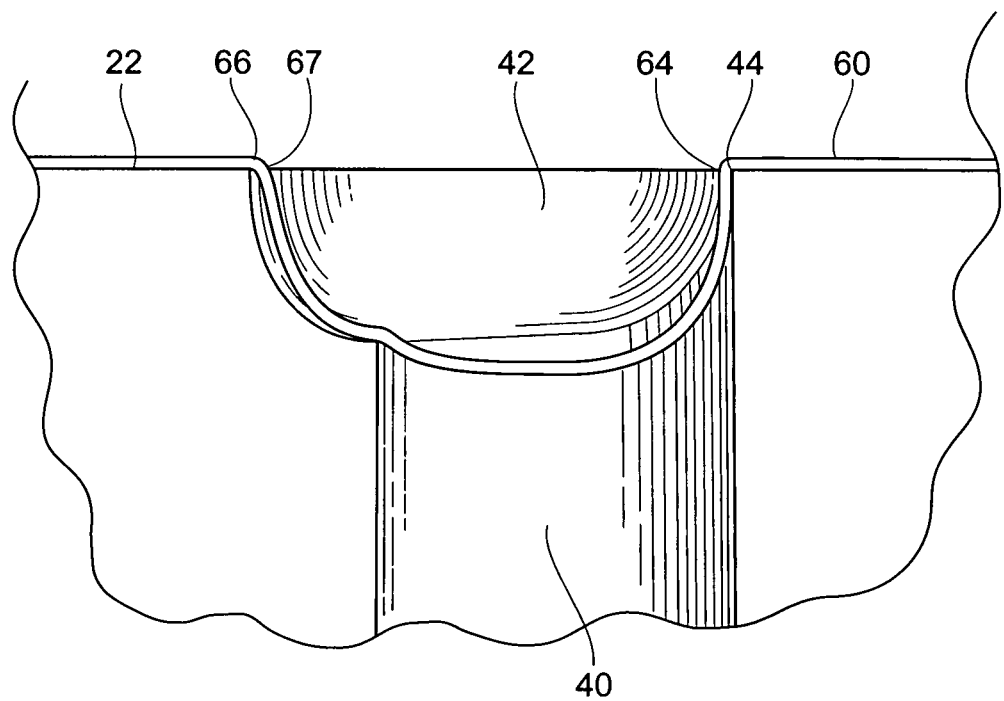

FIGS. 10A and 10B are a side elevation views, with portions cut away, of the vacuum wheel shown in FIG. 8.

The foregoing is considered as illustrative only of the principles of the invention. Furthermore, because numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of securing a stretchable piece of web material to a target web comprising:
    providing a first infeeding web of stretchable material;
    severing a discrete piece of said web of stretchable material from said infeeding web on a first drum rotating at a first tangential speed;
    setting said discrete piece of said web of stretchable material to a product pitch;
    stretching said discrete piece of said web of stretchable material a predetermined amount by transferring a leading edge of said discrete piece to a second drum rotating at a second tangential speed, faster than said first tangential speed, while a trailing edge of said discrete piece is carried by said first drum, to re-pitch said discrete piece of said stretchable material, to create a stretched discrete piece of said web of stretchable material;
    releasing said trailing edge of said stretched discrete piece of said web of stretchable material from said first drum to be carried by said second drum when a predetermined elongation percentage is achieved;
    transferring and stretching said stretched discrete piece of said web of stretchable material from said second drum to a third applicator drum operating at a third tangential speed, faster than said second tangential speed, to set a stretch percentage of said stretchable material;
    coupling said stretched discrete piece of said web of stretchable material to a target web.

* * * * *